United States Patent [19]

Elsey

[11] Patent Number: 4,854,309
[45] Date of Patent: Aug. 8, 1989

[54] FLEXIBLE WRIST SPLINT
[75] Inventor: Denise M. Elsey, Greensburg, Ohio
[73] Assignee: Akron City Hospital, Akron, Ohio
[21] Appl. No.: 190,876
[22] Filed: May 6, 1988
[51] Int. Cl.[4] ............................ A61F 5/04; A61F 13/00
[52] U.S. Cl. ................................ 128/87 R; 128/89 R; 128/165
[58] Field of Search ............... 128/87 R, 77, 78, 89 R, 128/16 S; 2/16; 273/189 A; D24/64

[56] References Cited
U.S. PATENT DOCUMENTS

| | | | |
|---|---|---|---|
| 3,238,939 | 3/1966 | Stubbs | 128/165 |
| 3,533,407 | 10/1970 | Smith | 128/165 |
| 3,804,084 | 4/1974 | Lehman | 128/165 |
| 3,935,858 | 2/1976 | Harroff | 128/165 |
| 4,047,250 | 9/1977 | Norman | 128/165 |
| 4,584,993 | 4/1986 | Nelson | 128/87 R |
| 4,716,892 | 1/1988 | Brunswick | 128/87 R |

Primary Examiner—Robert A. Hafer
Assistant Examiner—Michael Brown
Attorney, Agent, or Firm—Renner, Kenner, Greive, Bobak, Taylor & Weber

[57] ABSTRACT

A flexible wrist splint for the treatment of cumulative trauma disorder. The splint (10) can be worn on either wrist and is usable in the working environment. The splint includes a flexible panel (11) adapted to encircle the wrist area of a person, first and second opposed pockets (12,13) carried on the outer side (21) of the panel, flexible and resilient stays are (14) carried within the first and second pockets, an opening is (26) provided between the first and second opposed pockets for the insertion of a thumb, and fastening straps (15) for securing the panel about the wrist.

15 Claims, 4 Drawing Sheets

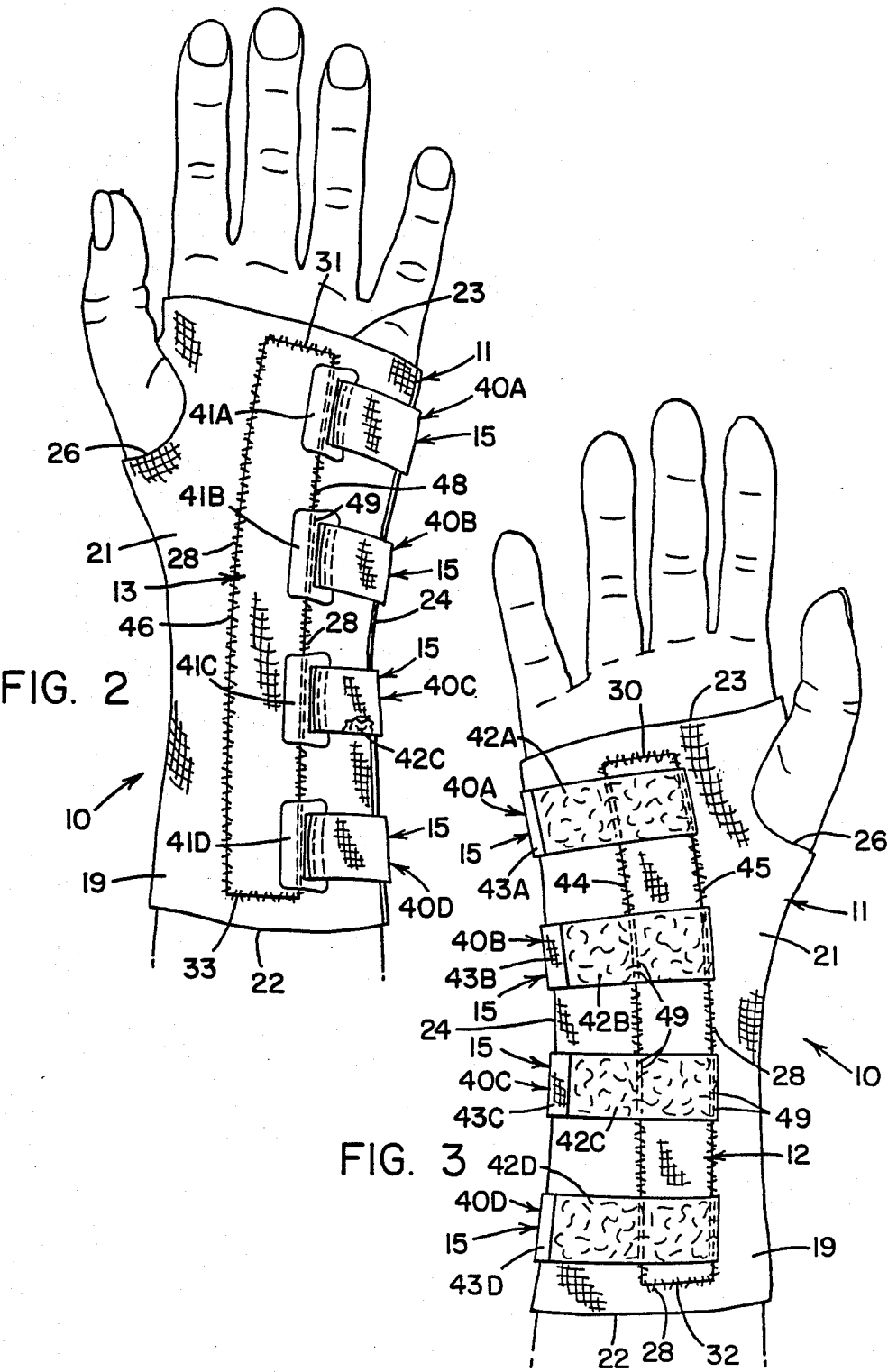

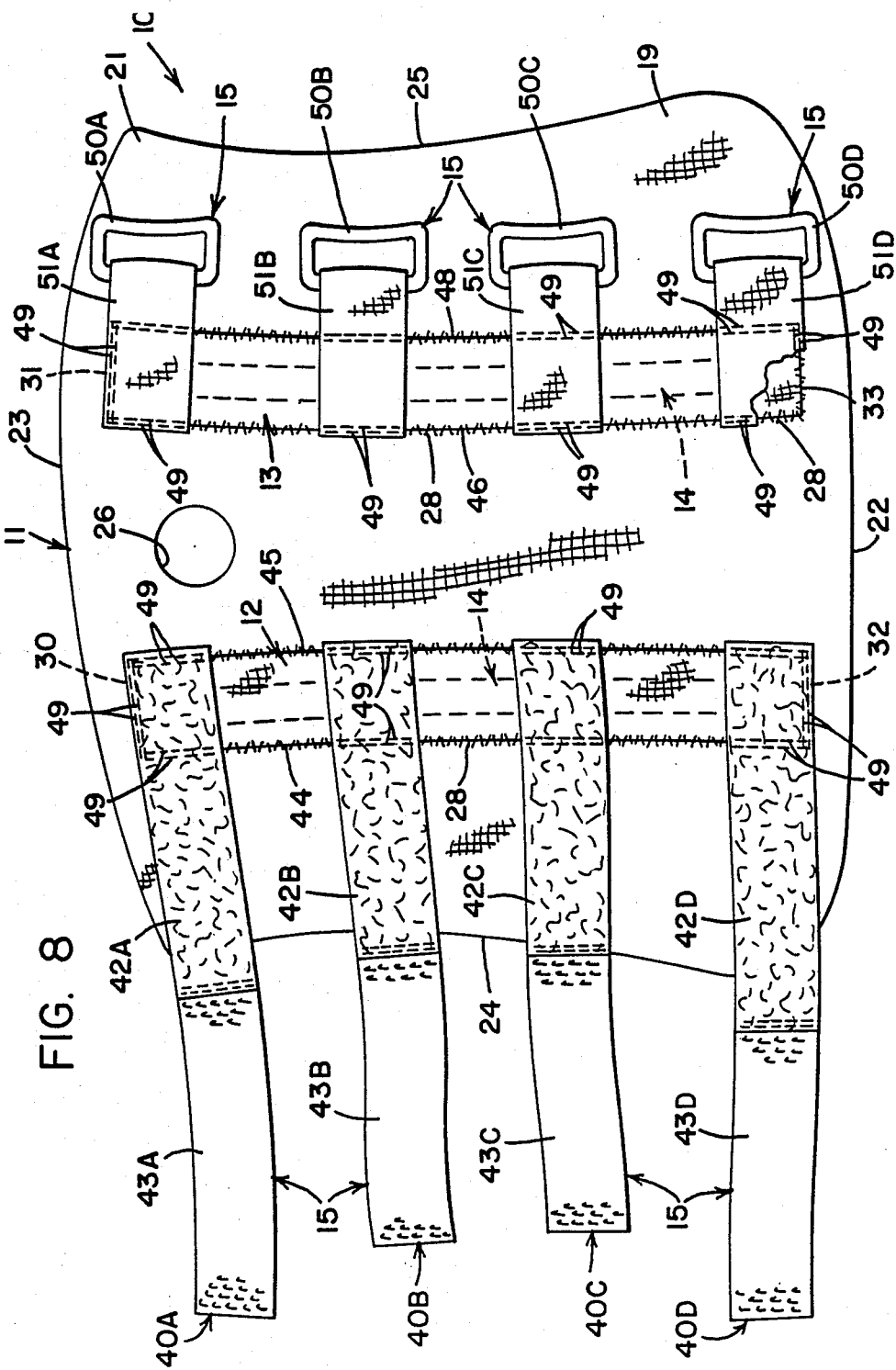

FLEXIBLE WRIST SPLINT

TECHNICAL FIELD

The present invention relates to a splint for the wrist which can be worn during work in industrial settings to discourage cumulative trauma disorder (CTD). This disorder has been well documented in the literature and has been identified as a major cause of lost time and worker compensation claims in automated industry.

Depending upon the work involved, afflicted workers exhibit symptoms of one or more disorders such as tennis elbow, carpal tunnel syndrome, ulnar nerve entrapment and tenosynovitis. To overcome these problems, the worker can perform exercises; he or she is told to avoid or minimize the type of repetitive movement that is causing the problem; he or she can be fitted with a splint, and in extreme cases resort may be made to surgery.

Splints are provided to support the wrist while at rest which are of a rigid type to be worn away from work. Other splints are provided to support the wrist during work which are of flexible type. To be of maximum usefulness, the flexible wrist splint must not hinder the use of the hand and, therefore, bulk of the splint and the amount of support must be balanced with freedom of hand movement during all repetitive activities so as to allow the worker the usual dexterity, strength and mobility of the uninjured worker.

BACKGROUND ART

A plethora of splints have been designed for total immobility of the wrist, to treat fractures and breaks, for limited immobility of the wrist to treat less severe injuries such as various CTD's, and as flexible devices to provide some level of support to assist movement of the injured wrist. In the area of flexible splints, U.S. Pat. No. 2,287,821 provides an early design of flexible support for the wrist and distal forearm. The support comprises several layers of chamois and leather stitched together and provided with straps and fastening buckles at opposite ends. The support includes a medial portion which flexes at the wrist but it lacks any type of stay and does not encompass the thumb.

U.S. Pat. No. 4,040,632 is directed toward a sports training aid which fits over the back of the hand, the wrist and the lower portion of the forearm and prevents bending of the wrist without interfering with the gripping capability of the hand. The device is essentially U-shaped with one leg of the "U" wrapping around the wrist and one around the hand between the thumb and forefinger. The two legs then fasten to the base of the "U" by Velcro. A support or reinforcing member 25 is provided in a pocket within the base 12 of the device and prohibits bending of the wrist.

U.S. Pat. No. 4,183,098 discloses a wrist support apparatus used as a sports aid which allows flexing in one direction while limiting it in the other. It employs two rigid plates connected by a hinge which are enclosed in an envelope having straps to hold the device in place on the arm. The straps wrap around the palm of the hand and the forearm and may be secured by Velcro. The hinges may be adjusted to allow extension of the wrist wherein the back of the hand moves toward the top of the forearm. Downward flexing or flexion, wherein the palm moves toward the bottom of the arm, is not restrained.

U.S. Pat. No. 4,441,490 presents an essentially triangular wrist brace wherein the top of the triangle extends across the back of the hand while the two base members wrap around the wrist and are secured by Velcro straps. The top member is also secured by Velcro straps running around the palm. A reinforcing member is provided on the dorsal surface of the hand and wrist and is a rigid strip of metal or plastic. This brace is intended to apply external pressure over the wrist and dorsal section of the hand to relieve tension exerted during physical activity. It may also be employed to provide support during the healing period after an injury.

U.S. pat. No. 4,584,993 provides a flexible wrist brace used for support during physical activity. The elastic wrap-around brace is provided with a number of stays on the proximal side for added support to the proximal or planar side of the wrist. The device is formed into a sleeve with proximal and distal sides closely encompassing the proximal and distal sides of a wrist with the elastic material in tension. Velcro straps are used to secure the device in place.

Finally, U.S. Design Pat. No. D-259,995 discloses a wrist brace that appears to be a fingerless glove having a single Velcro strap around the wrist. It extends from the back of the hand and the palm area, to a point somewhere along the lower forearm and no support stays are depicted.

Despite the existence of many splints and braces for the wrist area that have employed elastic materials and reinforcing stays, none have been useful in the treatment of work related conditions such as carpel tunnel syndrome. Such a device should be capable of use in the work environment and not interfere with the necessary movements of the hand and wrist.

DISCLOSURE OF THE INVENTION

It is therefore an object of the present invention to provide a wrist splint that is useful in the treatment of cumulative trauma disorder.

It is another object of the present invention to provide a wrist splint that is flexible and which can be worn while working.

It is yet another object of the present invention to provide a wrist splint that is elastic and can be tensioned about the wrist.

It is another object of the present invention to provide a wrist splint that provides two separate rates of expansion as it moves with the wrist.

It is still another object of the present invention to provide a wrist splint that employs a foam core for comfort and insulation of the wrist.

These and other objects together with the advantages thereof over the prior art, which shall become apparent from the specification which follows, are accomplished by the invention as hereinafter described and claimed.

In general, a wrist splint according to the present invention includes flexible panel means adapted to encircle the wrist area of a person and having inner and outer side, proximal and distal edges and lateral edges. The splint further comprises first and second opposed pockets carried on the outer side extending between the proximal and distal edges, flexible and resilient stay means carried within the first and second pockets, means provided between the first and second opposed pockets for the insertion of a thumb and, fastening means for securing the panel about the wrist, maintaining the inner side thereagainst.

BRIEF DESCRIPTION OF THE DRAWINGS

FIG. 2 is a top plan view of the wrist splint of the present invention depicting its position on the distal side of the wrist;

FIG. 3 is a bottom plan view of the wrist splint of the present invention depicting its position on the proximal side of the wrist;

FIG. 8 is a top plan view of the wrist splint of the present invention depicting an alternate embodiment of fastening means.

PREFERRED EMBODIMENT FOR CARRYING OUT THE INVENTION

Figure 1:
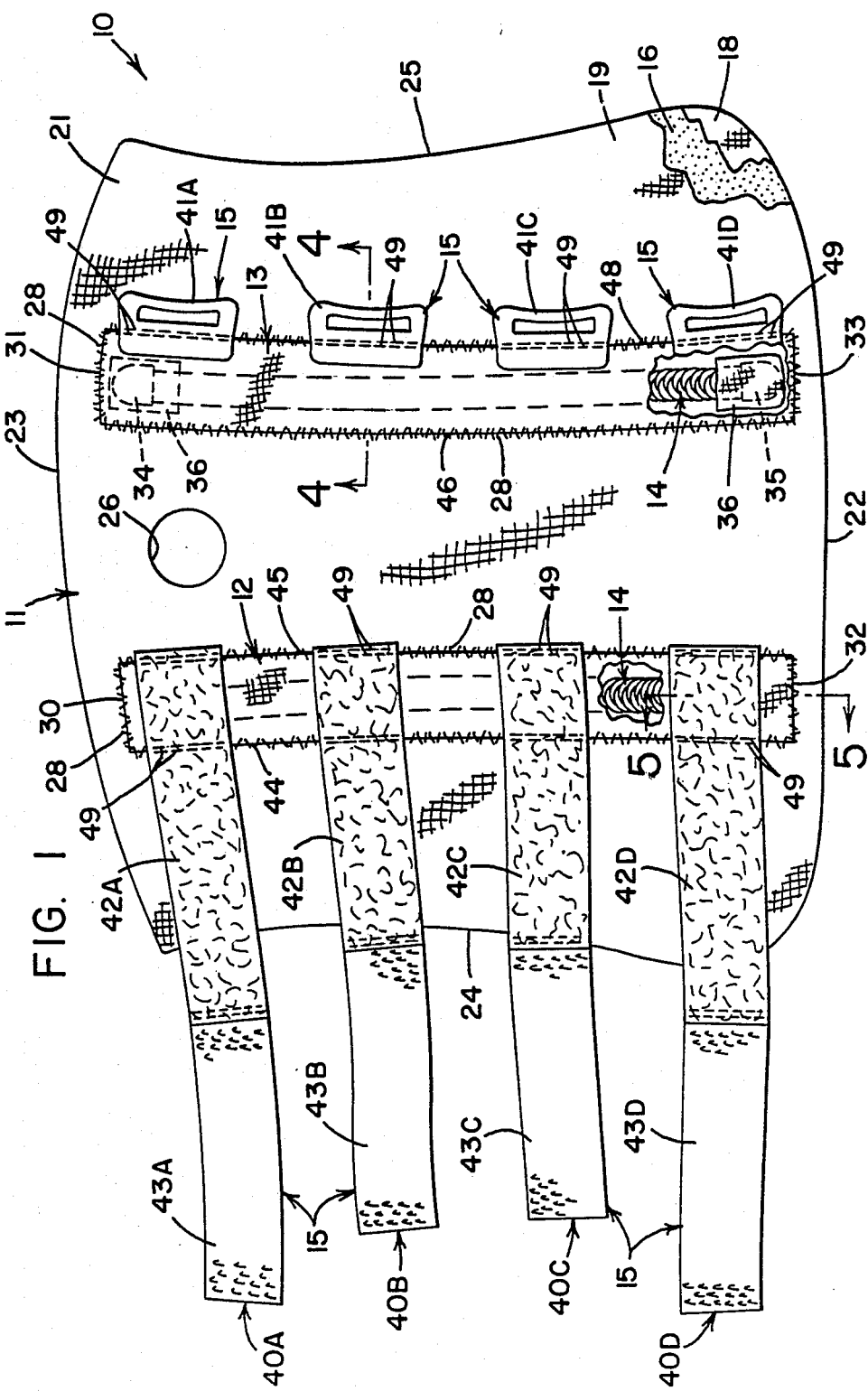
FIG. 1 is a top plan view of the wrist splint of the present invention.

A flexible wrist splint embodying the concepts of the present invention is designated generally by the numeral 10 on the attached drawings. The splint comprises generally, a flat panel 11, first and second opposed pockets 12 and 13, stay means 14, carried within each pocket and, fastening means 15 for securing the panel about the wrist.

Figure 4:
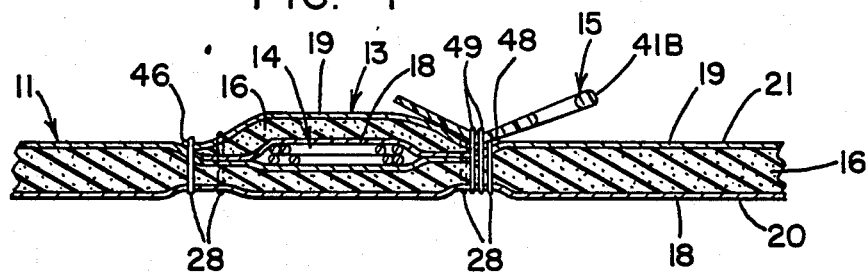
FIG. 4 is an enlarged section, taken substantially along line 4—4 of FIG. 1.

The panel 11 is generally flat and comprises three separate layers: an inner core 16 of a flexible and elastomeric foam, such as Neoprene (FIG. 4) and surface skin layers 18 and 19 which are applied to both sides of foam core 16. Both are made of a washable, expandable fabric such as nylon and are suitably bonded to the foam core 16 with an adhesive. It should be understood that lower skin 18 forms the inner side 20 of panel 11 and will contact the wrist area of a person when the splint is worn and that the supper skin 19 forms the outer side 21 of panel 11, providing a durable outer surface for the splint. The skins 18 and 19 protect the foam core while the expandable nature thereof contributes to the support of the wrist. The foam core is approximately one eighth inch (3 mm) thick and the skins are approximately one-thirty second inch (0.8 mm) thick. The panel is expandable up to about 100 percent.

The panel 11 additionally provides proximal and distal edges 22 and 23, respectively, and opposed lateral edges 24 and 25 which overlap slightly when the splint is worn on the wrist. A hole 26 is provided through the panel 11 near the distal edge for insertion of the thumb when the splint is mounted on the wrist.

The opposed pockets 12 and 13 are positioned on either side of the thumb hole 26 and are generally parallel to lateral edges 24 and 25. Each is approximately equidistant from the thumb hole and slightly closer thereto than to the edges 24 and 25. The pockets comprise the same structure as the panel 11, viz. a foam core 16 and surface skin layers 18 and 19 and are rectangular in shape. Each is fastened to the outer side 21 of panel 11 in a suitable manner such as stitching 28. The distal ends 30 and 31 of pockets 12 and 13 terminate beyond the thumb hole 26 and a short distance from distal edge 23. Similarly, the proximal ends 32 and 33 of pockets 12 and 13 terminate approximately the same short distance from proximal edge 22.

Figure 5:
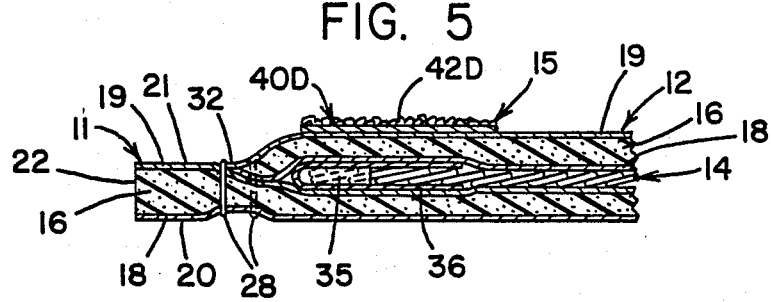
FIG. 5 is a section, taken substantially along line 5—5 of FIG. 1.

Each pocket is provided with a resilient, flexible stay 14 which comprises a flattened meal helix or spring, depicted in FIGS. 1 and 5. Although the stay is located within the pockets 12 and 13, it is not directly affixed to the panel 11 or the pocket. At the ends of each stay are provided metal tabs 34 and 35 which protect the pocket from being torn by the stay. Optionally, a strip 36 of flexible reinforcement, such as nylon or other plastic or cloth can be wrapped over the tabs 34 and/or 35 and a portion of the stay 14, as depicted in FIG. 5, as a further protection. During manufacture each pocket is sewn or otherwise affixed to the panel 11 and a stay, with optional reinforcement strips 36, at one or both ends, is placed and sealed therein. Of course, the stay 14 may comprise other forms and materials rather than the flattened metal helix depicted.

The fastening means 15 include a plurality of strips 40A–40D and a like plurality of fastening rings 41A–41D, each strip and mating ring forming a like pair. The fastening means preferably comprise a quick fastening/removal design such as Velcro. Accordingly, each strip 40A–40D includes a loop segment 42A–42D and a hook segment 43A–43D. The strips are mounted generally perpendicularly to one of the pockets 12 as depicted in FIG. 1, and are sewn along both longitudinal seams 44 and 45 of the pocket with stitching 49. The strips 40A–40D are nonelastic so that when the splint is worn, the panel is stretched around the wrist joint and remains in tension. The rings, which are a rigid plastic or similar material, are mounted generally perpendicular to the other pocket 13 and are sewn along one seam 48 of longitudinal seams 46 and 48 with stitching 49.

The first pair of fastening means 15, strip 40A and ring 41A, is located in alignment with the thumb hole 26 and extends slightly thereabove, as depicted in FIG. 1. The fourth pair, strip 40D and ring 41D, is located at approximately the same distance away from the proximal edge 22 as is the first pair from distal edge 23. The remaining pairs 40B–41B and 40C–41C are spaced equidistant between the first and fourth pairs. If desired the splint may provide only three pairs of fastening means, preferably by deleting the fourth pair 40D–41D, and employing the first three. It is important, however, that the first pair 40A–41A be located as depicted in FIG. 1 although the other pairs can be moved closer to the proximal edge 22.

While the splint can be provided with various numbers of paired strips and rings, three or four pairs as described herein are preferred. Similarly, the design should not be limited to Velcro type fasteners as buckles, snaps, buttons or the like could be substituted therefor. Velcro is the material of choice because it combines speed and ease of use with a wide range of adjustability.

An alternative embodiment of fastening means is depicted in FIG. 8. The splint 10 and component elements bearing the same numerals are identical to those elements discussed hereinabove and accordingly, it is not necessary to repeat their description here. The primary difference is the location of the fastening means 15 and the component elements thereof.

With reference to the left side of FIG. 8, fastening means 15 again comprise a plurality of strips 40A–40D of Velcro or similar material. Accordingly, each strip 40A–40D includes a loop segment 42A–42D and a hook segment 43A–43D. While the strips are mounted generally perpendicularly to one pocket 12, and are sewn along both seams 44 and 45 with stitching 49, the loop segment 42A of first strip 40A covers the distal end 30 of pocket 12 and carries stitching 49 thereover. Similarly, the loop segment 42D of last strip 40D covers the proximal end 32 of pocket 12 and carries stitching 49 thereover. The location of loop segments 42A and 42D over pocket ends 30 and 32 reinforces the pocket ends further in which instance the optional reinforcement strips 36 can be omitted.

With reference to the right side of FIG. 8, a plurality of fastening rings 50A–50D are provided, matable with strips 40A–40D, respectively. Each ring 50A–50D is fastened to panel 11 by means of a doubled over strap 51A–5D which is in turn stitched over pocket 13. Strap 51A contains stitching 49 along longitudinal seams 46 and 48 as well as distal edge 31 of pocket 13. Similarly, strap 51D is stitched at 49 along both longitudinal seams 46 and 48 as well as proximal edge 33 of pocket 13. Straps 51B and 51C are stitched at 49 along both longitudinal seams. In this manner, the rings are in effect secured by double stitching along the pocket 13 to the panel 11. Also, the ends of pocket 13 are further reinforced by straps 51A and 51D which can eliminate the use of reinforcing strips 36.

Application of the splint 10 is performed by inserting the thumb through the hole 26 and wrapping the wrist with the panel 11, maintaining the inner side 20 against the wrist. The splint can be provided in a variety of sizes, varying by length and width, so that when correctly fitted, a pocket and stay is provided medially over the wrist as depicted in FIG. 2 and medially over the palm and underside of the wrist, as depicted in FIG. 3. The thumb hole assists in proper placement and also holds the splint while it is wrapped about the wrist. Proper tensioning of the elasticity is achieved by allowing the lateral edges 24 and 25 to overlap slightly. In this manner the wrist is supported during flexion and extension as well as lateral movement.

As also depicted in FIGS. 2 and 3, the splint 10 is dimensioned so that approximately one-half or less of its overall length extends above the wrist joint, while the remaining one-half or more extends below the wrist joint and over the lower forearm. The distal edge 23 extends to approximately the upper one-third of the hand (FIG. 3) so that the grip is not impaired, nor is movement of the thumb and fingers. The upper or distal ends of pockets 12 and 13 terminate above the web formed between the thumb and the hand and it is noted that the first pair of fastening means 15 is located across from and slightly above the thumb. Furthermore, the first two pairs, 40A–41A and 40B–41B are located above the wrist joint, generally above and below the thumb, as seen in the drawings.

Figure 6:
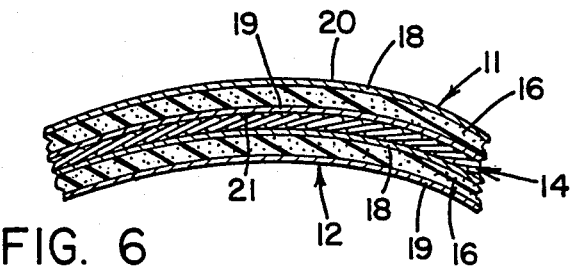
FIG. 6 is a fragment view in section depicting a segment of the wrist splint in flexion.
Figure 7:
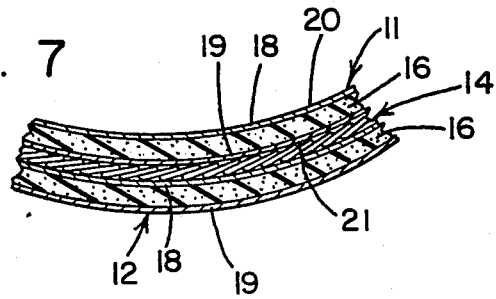
FIG. 7 is a fragment view in section depicting a segment of the wrist splint in extension.

The foam core 16 provides a degree of comfort that would not be present if the panel comprised only one or both of the expandable skins, 18 or 19. It also helps to keep the wrist area warm is an advantage to workers exposed to cold environments. Additionally, the foam core allows the skins 18 and 19 to elongate and contract at two different rates during flexion and extension of the wrist. With reference to FIGS. 6 and 7, a cross-section of the splint 10 through the wrist area is depicted. Assuming the splint is mounted on the right wrist as in FIG. 3, then the pocket 12 is on the palm or underside of the wrist and FIG. 6 shows the panel when the wrist is in flexion.

In this position, the inner skin 18 is elongated to a greater degree relative to outer skin 19 in order to accommodate the movement. The foam core 16 is acted upon in two different directions, extending at the interface with the inner skin 18 and compressing at the interface with the outer skin 19. In FIG. 7, the splint is in the position occupied when the wrist is extended and the outer skin 19 is now elongated to a greater degree relative to the inner skin 18.

Splints 10, manufactured in accordance with the foregoing description were used and evaluated on a large scale basis in several industrial settings including the processing and packaging of poultry and ham, where the temperature is generally below ambient, and the plastics and rubber business where the temperature is generally at or greater than ambient. At each site, the splints were given to multiple employees who had previously reported discomfort of their wrists and hands. In the poultry industry, for instance, processing equipment allows for sizing and cutting of birds at a rate of over 100 per minute. Employees were found to suffer from carpal tunnel syndrome, a pressure on the median nerve of the wrist, and tennis elbow which is characterized by pain over the lateral aspect of the elbow and by radiation of pain down the forearm. The pain is aggravated by any activity that puts tension on the forearm.

Splints were worn on one or both affected wrists by each employee during the work day. The splints were employed as a conservative measure to discourage the onset of cumulative trauma disorders. The subjects reported a decrease of the symptoms of numbness and pain in their hands and a benefit from the stability the splint provided at the wrist while allowing the wrist to flex and extend readily in the performance of their job duties.

Two groups of employees suffering from carpal tunnel syndrome were also evaluated. One group was referred, following surgical release, and was given the splint as the postoperative recovery program. The other group was referred for conservative management to discourage the disorder from developing further. Both groups reported that the splint provided the flexible support they required during their discomfort.

Based upon the foregoing description, it should now be evident that the splint of the present invention satisfies the objects set forth hereinabove and is useful in treating workers afflicted with various cumulative trauma disorders. Although one preferred embodiment has been set forth, it is to be understood that the splint can be manufactured in other manners and thus, the present invention should not be limited to the use of a particular flexible stay, or sewn pockets, or the use of Velcro straps and fastening rings. Thus, the scope of the invention shall include all modifications and variations that fall within the scope of the attached claims.

I claim:

1. A flexible wrist splint comprising:
    flexible panel means adapted to encircle the wrist area of a person, said panel means having inner and outer sides, proximal and distal edges, opposed lateral edges and first and second expandable skin layers and a foam core therebetween;
    first and second opposed pockets carried on said outer side extending between said proximal and distal edges;
    said first and second opposed pockets having first and second expandable skin layers and a foam core therebetween;
    flexible and resilient stay means carried within said first and second pockets;
    means provided between said first and second opposed pockets for the insertion of a thumb;

said means for inserting of a thumb being a hole in said flexible panel means;

fastening means for securing said panel means about the wrist, maintaining said inner side thereagainst;

said fastening means being contiguously affixed with said first and second opposed pockets and further being a plurality of strips affixed along at least one edge of said first pocket and a like plurality of rings are affixed along one edge of said second pocket engageable with said strips, each said strip and ring forming a pair; and said hole for the insertion of a thumb being located between one said strip and one said ring of one said pair.

2. A flexible wrist splint, as set forth in claim 1, wherein said strips and rings are substantially perpendicular to said first and second pockets.

3. A flexible wrist splint, as set forth in claim 2, wherein said strips provide interlocking hook and loop fastening elements, approximately one-half of said strip carrying one of said hook or loop fastening elements; the other one-half of said strip carrying the other of said hook or loop fastening elements.

4. A flexible wrist splint, as set forth in claim 3, having at least four pairs of strips and rings.

5. A flexible wrist splint, as set forth in claim 4, wherein said rings are secured by straps affixed along at least one edge of said second pocket.

6. A flexible wrist splint, as set forth in claim 5, wherein said first pair of strips and rings covers and reinforces said distal ends of said first and second opposed pockets and said fourth pair of strips and rings covers and reinforces said proximal ends of said first and second pockets.

7. A flexible wrist splint, as set forth in claim 6, wherein each said strip is affixed along two edges of said first pocket and each said strip is affixed along two edges of said second pocket.

8. A flexible wrist splint, as set forth in claim 1, having at least three pairs of strips and rings, a first pair being adjacent said distal edge, a second pair being closer to said proximal edge than said distal edge and said third pair being positioned therebetween.

9. A flexible wrist splint, as set forth in claim 6, wherein said for the insertion of a thumb is located between a strip and a loop of said first pair.

10. A flexible wrist splint, as set forth in claim 9, wherein said means for insertion of a thumb is located between said first and second pair of fastening means.

11. A flexible wrist splint, as set forth in claim 10, wherein said first and second pair of fastening means are distal to the wrist when said splint is positioned thereon.

12. A flexible wrist splint, as set forth in claim 1, wherein each said strip is affixed along two edges of said first pocket.

13. A flexible wrist splint, as set forth in claim 1, wherein one of said opposed lateral edges overlaps said other edge when said splint is positioned on the wrist.

14. A flexible wrist splint, as set forth in claim 1, having a length sufficient to extend to the upper one-third of the hand when positioned on the wrist and to extend below the wrist at least an equal distance.

15. A flexible wrist splint, as set forth in claim 1, wherein said skin layers are expandable at different rates during flexion and extension of the wrist.

* * * * *

UNITED STATES PATENT AND TRADEMARK OFFICE
CERTIFICATE OF CORRECTION

PATENT NO. : 4,854,309  Page 1 of 2
DATED : August 8, 1989
INVENTOR(S) : Denise Muffly Elsey It is certified that error appears in the above-identified patent and that said Letters Patent is hereby corrected as shown below:

Column 2, line 22, "D-259,995" should read --D-259,955--; line 60, "side" should read --sides--

Column 3, line 41, "supper" should read --upper--

Column 4, line 2, "meal" should read --metal--; lines 30-31, "perpendicular" should read --perpendicularly--

Column 5, line 12, "51A-5D" should read --51A-51D--; line 55, "area warm is" should read --area warm which is--

Column 6, line 16, "at a rate" should read --at the rate--

Claim 1, Column 7, line 1, "inserting" should read --insertion--

Claim 7, Column 8, line 5, "strip" should read --strap--

UNITED STATES PATENT AND TRADEMARK OFFICE
CERTIFICATE OF CORRECTION

PATENT NO. : 4,854,309

DATED : August 8, 1989

INVENTOR(S) : Denise M. Elsey

It is certified that error appears in the above-identified patent and that said Letters Patent is hereby corrected as shown below:

Claim 9, column 8, line 13, "said for" should read --said hole for--

Signed and Sealed this

Twenty-ninth Day of January, 1991

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,854,309

DATED : August 8, 1989

INVENTOR(S) : Denise Muffly Elsey

It is certified that error appears in the above-identified patent and that said Letters Patent is hereby corrected as shown below:

On the title page, item [75], "Denise M. Elsey" should read
--Denise Muffly Elsey--.

Signed and Sealed this

Fourteenth Day of May, 1991

*Attest:*

HARRY F. MANBECK, JR.

*Attesting Officer*

*Commissioner of Patents and Trademarks*